United States Patent
Twining et al.

(10) Patent No.: US 12,311,419 B2
(45) Date of Patent: May 27, 2025

(54) GREEN CREMATION

(71) Applicant: Endure Products, LLC, Dripping Springs, TX (US)

(72) Inventors: Ronald Fremont Twining, Dripping Springs, TX (US); Omar Besim Hakim, Dripping Springs, TX (US)

(73) Assignee: Endure Products, LLC, Dripping Springs, TX (US)

( * ) Notice: Subject to any disclaimer, the term of this patent is extended or adjusted under 35 U.S.C. 154(b) by 0 days.

(21) Appl. No.: 18/299,872

(22) Filed: Apr. 13, 2023

(65) Prior Publication Data

US 2023/0249233 A1    Aug. 10, 2023

Related U.S. Application Data

(60) Provisional application No. 63/330,580, filed on Apr. 13, 2022.

(51) Int. Cl.
| | | |
|---|---|---|
| *B09B 3/00* | (2022.01) | |
| *A01K 67/30* | (2025.01) | |
| *A61G 17/00* | (2006.01) | |

(52) U.S. Cl.
CPC ............... *B09B 3/00* (2013.01); *A01K 67/30* (2025.01); *A61G 17/002* (2013.01)

(58) Field of Classification Search
CPC ........ B09B 3/00; A61G 17/00; A61G 17/002; A61G 17/04; A61G 17/048; A01K 67/033; A01K 1/0245
See application file for complete search history.

(56) References Cited

U.S. PATENT DOCUMENTS

| | | | | |
|---|---|---|---|---|
| 3,257,820 | A * | 6/1966 | Case | F25D 3/105 27/11 |
| 4,723,418 | A * | 2/1988 | Whitmer, II | F25D 15/00 62/298 |
| 5,924,181 | A * | 7/1999 | Takasugi | A01N 1/00 27/11 |
| 11,439,559 | B2 * | 9/2022 | Jenkins | A61G 17/048 |
| 2010/0213292 | A1 * | 8/2010 | Sullivan | A61G 17/0136 27/3 |
| 2013/0178687 | A1 * | 7/2013 | Wilson | B09B 3/00 422/184.1 |
| 2014/0014750 | A1 * | 1/2014 | Cho | B09B 3/00 241/68 |
| 2022/0272955 | A1 * | 9/2022 | Martínez Escribano et al. | A01K 67/033 |
| 2022/0304289 | A1 * | 9/2022 | Jansen | A01K 67/033 |
| 2022/0314288 | A1 * | 10/2022 | Bar | B09B 3/00 |

(Continued)

*Primary Examiner* — William L Miller
(74) *Attorney, Agent, or Firm* — DICKINSON WRIGHT PLLC

(57) ABSTRACT

Systems for cremating a body. The system includes a box assembly and a vessel. The box assembly is for storing the body or a portion of a body. The box assembly includes a box defining a box cavity, a bottom end, a top end, and at least one side wall extending from the bottom end to the top end. The box assembly also includes an air conditioner disposed in the box cavity. The air conditioner is configured to control a temperature level or a humidity level in the box cavity. The vessel is coupled to the at least one side wall of the box. The vessel includes insect larvae that self-harvest, exit the vessel, and enter the box assembly to decompose the body or the portion of the body stored in the box assembly.

18 Claims, 5 Drawing Sheets

(56) References Cited

U.S. PATENT DOCUMENTS

2023/0310248 A1\* 10/2023 Liu ........................ A61G 17/00
  27/21.1
2024/0008462 A1\* 1/2024 Munk-Bogballe ... A01K 67/033

\* cited by examiner

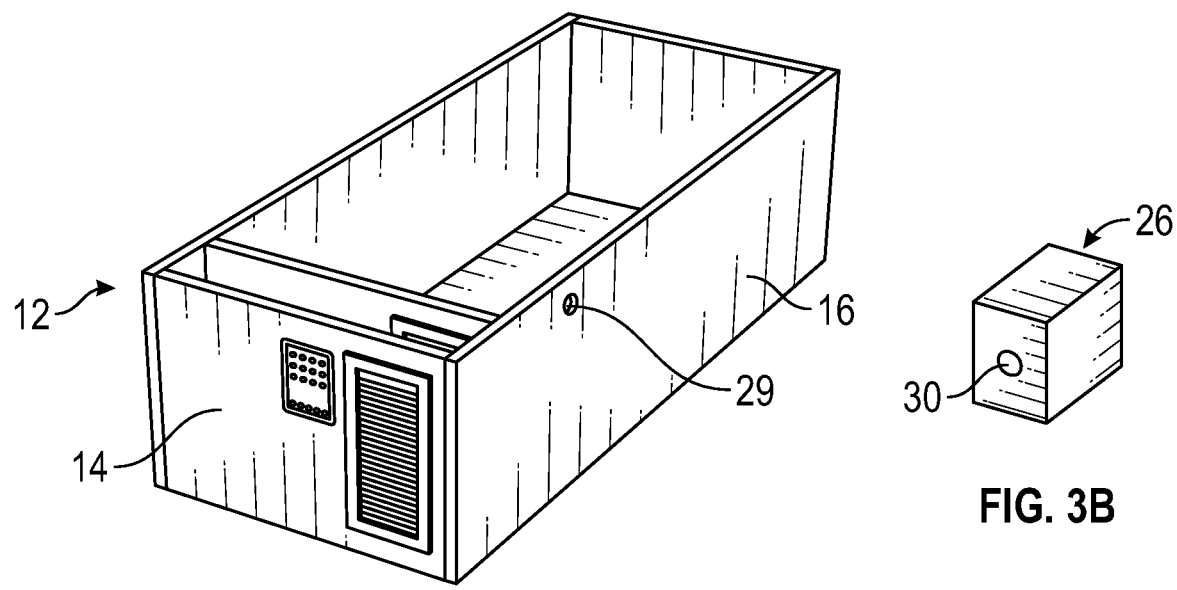
FIG. 3A
FIG. 3B
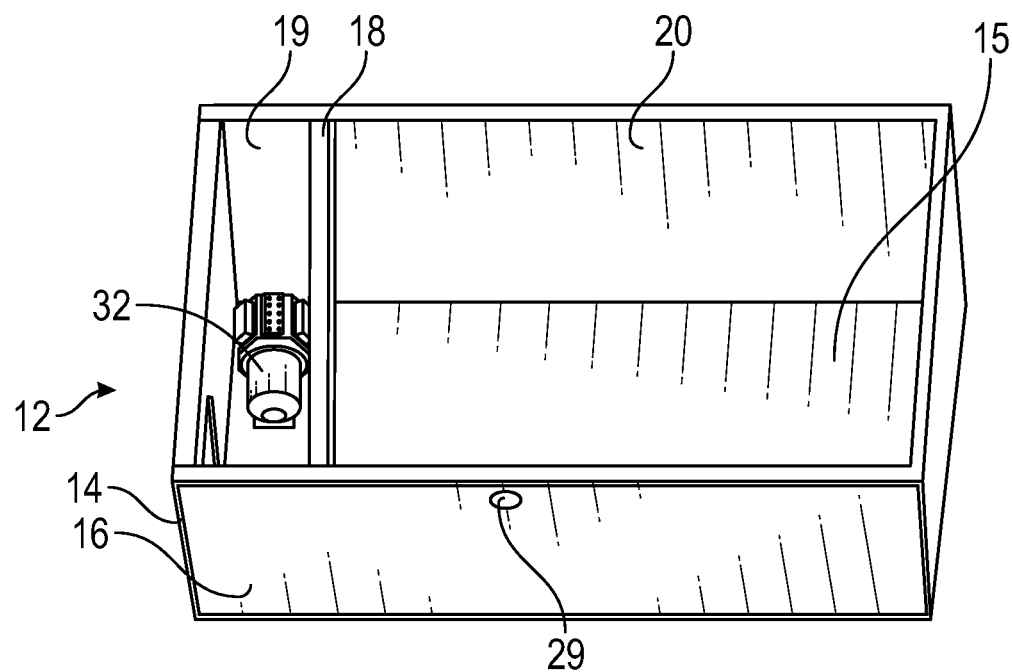
FIG. 3C

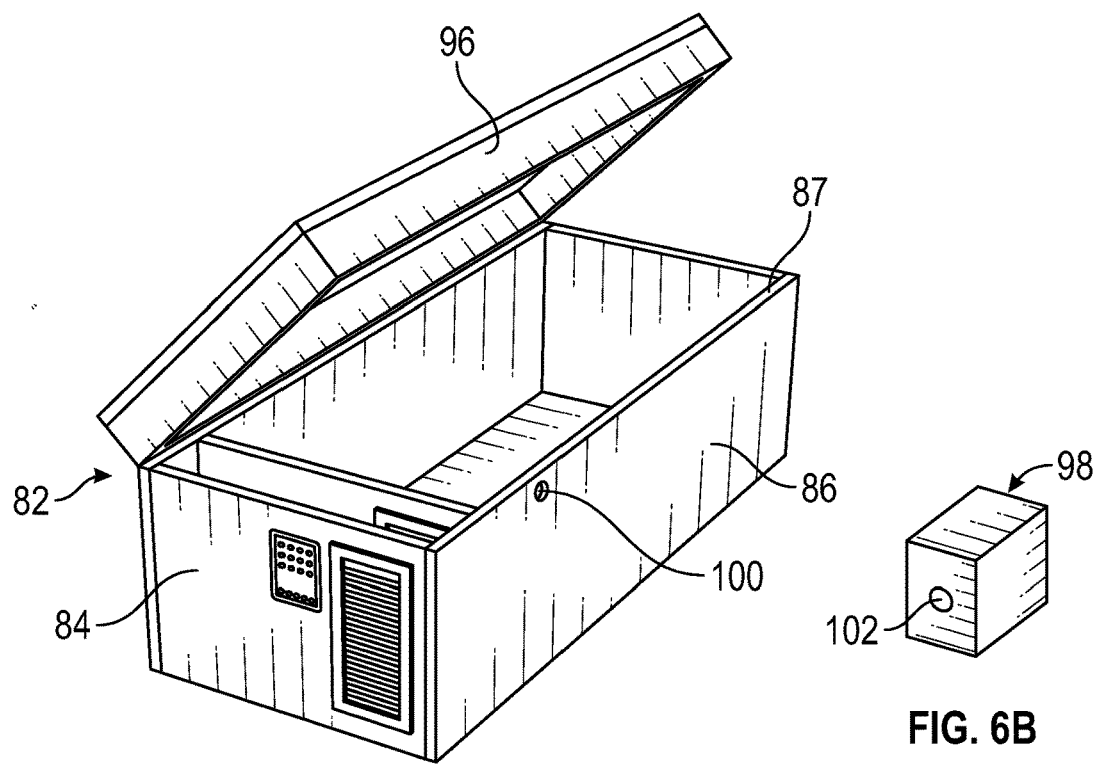
FIG. 6A
FIG. 6B
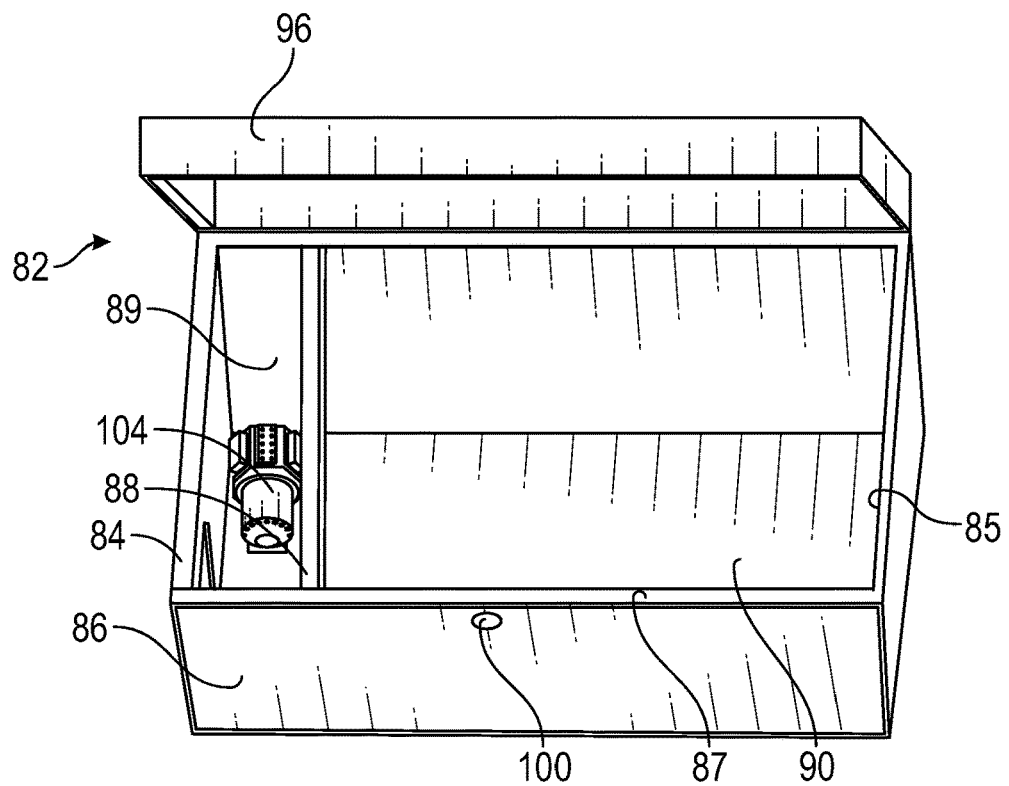
FIG. 6C

GREEN CREMATION

CROSS-REFERENCE TO RELATED APPLICATIONS

This application claims priority to and the benefit of U.S. Provisional Application No. 63/330,580 filed Apr. 13, 2022, titled "GREEN CREMATION," the entire disclosure of which is hereby incorporated by reference for all purposes.

TECHNICAL FIELD

The present disclosure relates to green cremation and more specifically, green cremation using insect larvae.

BACKGROUND

Over the years, flame-based cremations have surpassed burials as a primary choice to dispose deceased bodies, including human and animal bodies. Although this type of cremation is less harmful than burials, cremation still has negative impacts on the environment. For example, because flame-based cremation typically requires fuel to cremate bodies, it releases a considerable amount of carbon dioxide into the air. Therefore, there is a need for a more gentle, eco-friendly, and carbon-neutral method for cremation.

SUMMARY

Disclosed herein are implementations of a green cremation system. The present disclosure provides a system for cremating a body including, in one implementation, a box assembly and a vessel. The system may be situated in an environment whose conditions are controllable. The box assembly is for storing the body or a portion of the body. The box assembly includes a box and an air conditioner. The box defines a box cavity within the box, a bottom end, a top end defining a box opening connected to the box cavity, and at least one side wall extending from the bottom end to the top end. The air conditioner is disposed within the box cavity. The air conditioner is configured to control a temperature level or a humidity level in the box cavity when the air conditioner is in operation. The vessel is coupled to the at least one side wall of the box of the box assembly. The vessel includes insect larvae that self-harvest, exit the vessel, and enter the box assembly to decompose the body or the portion of the body stored in the box assembly.

The present disclosure also provides a system for cremating a body including, in one implementation, a box assembly, a vessel, and a cover. The box assembly is for storing the body or a portion of the body. The box assembly includes a box and an air conditioner. The box defines a box cavity within the box, a bottom end, a top end defining a box opening connected to the box cavity, and at least one side wall extending from the bottom end to the top end. The air conditioner is disposed within the box cavity. The air conditioner is configured to control a temperature level or a humidity level in the box cavity when the air conditioner is in operation. The vessel is coupled to the at least one side wall of the box of the box assembly. The vessel includes insect larvae that self-harvest, exit the vessel, and enter the box assembly to decompose the body or the portion of the body stored in the box assembly. The cover is hingedly connected to or removably disposed onto the top end of the box of the box assembly. The system is in an open state when the cover uncovers the box cavity of the box. The system is a closed state when the cover covers the box cavity of the box.

Other technical features may be readily apparent to one skilled in the art from the following figures, descriptions, and claims.

BRIEF DESCRIPTION OF THE DRAWINGS

For a more complete understanding of the present disclosure and its advantages, reference is now made to the following description, taken in conjunction with the accompanying drawings. It is emphasized that, according to common practice, the various features of the drawings are not necessarily to-scale. On the contrary, the dimensions of the various features may be—and typically are—arbitrarily expanded or reduced for the purpose of clarity.

FIG. 3A depicts a schematic perspective view of the box assembly of the system as described in FIG. 1.

FIG. 3B depicts a schematic perspective view of the vessel as described in FIG. 1.

FIG. 3C depicts a schematic isometric view of the box assembly of the system as described in FIG. 1.

FIG. 6A depicts a schematic perspective view of the box assembly of the system as described in FIG. 5.

FIG. 6B depicts a schematic perspective view of the vessel as described in FIG. 5.

FIG. 6C depicts a schematic isometric view of the box assembly of the system as described in FIG. 5.

NOTATION AND NOMENCLATURE

Figure 1:
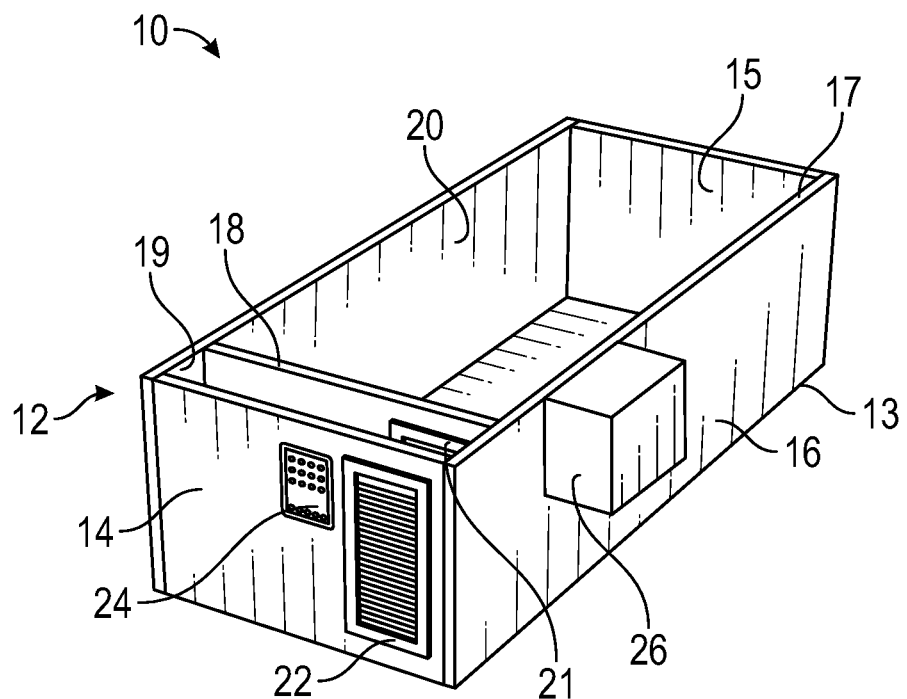
FIG. 1 depicts a schematic perspective view of a system for green cremation according to a first embodiment of the present disclosure.

Various terms are used to refer to particular system components. A particular component may be referred to commercially or otherwise by different names. Further, a particular component (or the same or similar component) may be referred to commercially or otherwise by different names. Consistent with this, nothing in the present disclosure shall be deemed to distinguish between components that differ only in name but not in function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices and connections.

The terminology used herein is for the purpose of describing particular example implementations only, and is not intended to be limiting. As used herein, the singular forms "a," "an," and "the" may be intended to include the plural forms as well, unless the context clearly indicates otherwise.

The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example implementations. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "up," "upper," "top," "bottom," "down," "inside," "outside," "contained within," "superimposing upon," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

DETAILED DESCRIPTION

The following discussion is directed to various implementations of the present disclosure. Although one or more of these implementations may be preferred, the implementations disclosed should not be interpreted, or otherwise used, as limiting the scope of the present disclosure, including the claims. In addition, one skilled in the art will understand that the following description has broad application, and the discussion of any implementation is meant only to be exemplary of that implementation, and not intended to intimate that the scope of the disclosure, including the claims, is limited to that implementation.

Aspects of the present disclosure relates to green cremation and more specifically, green cremation using insect larvae. In some implementations, the insect larvae may be black soldier fly larvae (BSFL). FIG. 1 depicts a schematic perspective view of a system for green cremation according to a first embodiment of the present disclosure. The system 10 may be situated in an environment whose conditions are controllable. The conditions of the environment may include parameters such as a temperature level, a humidity level, a moisture level, odors, and an amount of air. For example, the environment may be controlled to maintain at a certain temperature and/or humidity level as desired. In FIG. 1, the system 10 may include a box assembly 12 for storing at least one body or a portion of a body. The body may be a human body, a non-human (e.g., dog or cat) body, or an organ from a human or non-human body. The box assembly 12 may include a box 14 defining a box cavity 15 within the box 14. The box 14 may further include a bottom end 13 (e.g., a base), a top end 17 defining a box opening connected to the box cavity 15, and at least one side wall (e.g., side wall 16) extending from the bottom end 13 to the top end 17. The side wall 16 at least partially defines the box cavity 15. The side wall 16 may be made of a thermal insulation material. Although FIG. 1 depicts that the shape of the box assembly 12 is rectangular, it is contemplated that in one or more implementations of the present disclosure, the box assembly 12 may be in any other desired geometric shapes, including, but not limited to, round, square, oval, or polygonal. The box assembly 12 may further include a size to receive a body or a portion of the body therein.

As shown in FIG. 1, the box assembly 12 may further include an insert 18 disposed within the box cavity 15, which separates the box cavity 15 into a first chamber 19 and a second chamber 20. The insert 18 may be disposed at any location within the box cavity 15. In some implementations, the insert 18 may be connected to the side wall 16 of the box 14. In some other implementations, the insert 18 may be connectable to the side wall 16 of the box 14, in which case the insert 18 may be removable or replaceable. As shown in FIG. 1, the insert 18 may include an airway 21 through which air in the box cavity 15 may flow from the first chamber 19 to the second chamber 20, or vice versa. The airway 21 may be an opening disposed in the insert 18. In some implementations, a vent may be used to cover the opening and allow for the air in the box cavity 15 to flow between the first chamber 19 and the second chamber 20. The box assembly 12 may further include an air conditioner 32 (see FIG. 3C) disposed in the first chamber 19. The air conditioner 32 is configured to control a temperature level and/or a humidity level in the box cavity 15 when it is in operation. In some implementations, the air conditioner 32 may include one or more devices that control other environmental conditions within the box cavity 15 (e.g., moisture control and odors). The second chamber 20 may include a shape and a size to receive a body or a portion of the body therein for cremation as described herein.

Referring to FIG. 1, the box assembly 12 may further include an air vent 22 disposed on the side wall 16 of the box 14 thereof. The air vent 22 may be configured for air to be exchanged between the box cavity 15 and the environment in which the system is situated. For example, the air vent 22 may be configured for the air inside the box cavity 15 to exit the box assembly 12 or may be configured for the air in the environment to enter the box assembly 12.

In some implementations, the box assembly 12 may further include an ozone generator disposed on the side wall 16 of the box 14. The ozone generator (not shown) may be configured to remove odors from the box cavity 15. For example, the ozone generator may be disposed in an exhaust chamber with a one-way air valve. In such an implementation, the ozone generator is configured to remove odors from the box assembly 12 without exposing the insects in the box assembly 12 to ozone.

The box assembly 12 may also include an electronic control panel 24 connected thereto and configured to control the operation of the system 10, including the operation of the air conditioner 32. In some implementations, the electronic control panel 24 may be connected to the side wall 16 of the box 14. According to one or more implementations of the present disclosure, the electronic control panel 24 may be a display interface, through which an operator may input operating instructions to the system 10 for the purpose of controlling the conditions (e.g., a temperature level, a humidity level, or an air amount) within the box assembly 12. Upon a request by the operator, the electronic control panel 24 may display images or videos showing a scene of the box cavity 15. This allows the operator to monitor the operation of the system 10 in real time or near real time. The electronic control panel 24 may further electronically communicate with a remote server, such as a remote storage cloud, a remote control center, or a mobile phone of the operator or of any person of interest (e.g., a family member of the at least one body or portion(s) of the body). The electronic control panel 24 may also, by wires or wirelessly, connect to at least one another electronic control panel of another system of this kind. The connection between or among such systems may provide additional features, including, but not limited to, data sharing between or among the systems, remote controls of the systems, or alert notifications among the systems. For example, if there is a technical problem with one of the connected systems, the system having the technical problem may generate an alert, which may be sent to other connected systems or to a technician or an operator who may then fix the technical problem.

The electronic control panel 24 may also leverage the Internet of Things (IoT), Bluetooth, or Wi-Fi to remotely connect to, enable, and control one or more functionalities of the system 10. For example, the electronic control panel 24 may be configured to present a display interface on a remote device, through which a user may input operating instructions to the system 10 for the purpose of controlling the conditions within the box assembly 12 (e.g., a temperature, a humidity level, or an air amount).

To carry out green cremation according to this implementation of the present disclosure, the system 10 may further include a vessel 26 coupled to the side wall 16 of the box assembly 12. In some implementations, the vessel 26 may be glued, screwed, or hooked to the side wall 16 of the box assembly 12, or any other desired coupling mechanisms.

As shown in FIG. 1, the vessel 26 may be coupled to an outer surface of the side wall 16 of the box assembly 12. In some implementations, the vessel 26 may be integrated with the box assembly 12. In some other implementations, the vessel 26 may be removably attached to the box assembly 12. It is contemplated that although FIG. 1 shows one vessel coupled to the side wall 16 of the box assembly 12, more than one vessels may be similarly coupled thereto. The box assembly 12 may include a first orifice 29 (see FIG. 3A) on the side wall 16 thereof. The vessel 26 may include a second orifice 30 (see FIG. 3B), which may, with the first orifice 29, form a channel between the vessel 26 and the box assembly 12 when the vessel 26 is coupled to the box assembly 12. It is further contemplated that when more than one vessels coupled to the side wall 16 of the box assembly 12, the box assembly 12 may include more than one orifices on the side wall 16 thereof to accommodate the orifices on those vessels. In some other implementations, the vessel 26 may include more than one orifices in addition to the second orifice 30.

The vessel 26 may contain BSFL. The BSFL are hatched from eggs laid by adult female black soldier flies (BSF). After hatching, a larval development stage may begin, during which the BSFL may consume organic or inorganic matters (e.g., organic or inorganic waste in the vessel 26). The larval development stage may last about two or three weeks. Thereafter, the BSFL may mature into juvenile and/or adult larvae, which may later turn into adult black soldier flies (BSF). The adult BSF may then mate (e.g., in the air within the vessel 26), and adult female BSF may lay more eggs to harvest another generation of BSFL The adult BSF may live for a few more days, or a week or more, until they die.

The vessel 26 may contain, in addition to or independent from the BSFL, insect larvae from other insects including but not limited to blowflies, flesh flies, scorpion flies, dermestid beetles, carrion beetles, rove beetles, hister beetles, noctuid caterpillar, or a combination thereof. After hatching, a larval development stage may begin, during which the insect larvae may consume organic or inorganic matters (e.g., organic or inorganic waste in the vessel 26). Thereafter, the insect larvae may mature into juvenile and/or adult larvae, which may later turn into adult insects. The adult insects may then mate (e.g., in the air within the vessel 26), and adult female insects may lay more eggs to harvest another generation of insect larvae. For ease of understanding, the description describes green cremation using BSFL. However, it is to be understood that insect larvae from other insects, such as the ones described above, may be used.

The vessel 26 may include a shape and a size to allow the BSFL to self-harvest there within, as described herein. For example, the vessel 26 may include a shape and a size to allow the BSFL to establish one or more colonies there within. The vessel 26 may include a slanted wall having a slope angle so as to allow the BSFL to exit the vessel 26. If the slope angle is steep, the BSFL may not easily exit the vessel 26. On the other hand, if the slope angle is shallow, the BSFL may exit the vessel 26 at an early stage during the larval development stage, which is not helpful for establishing the colonies within the vessel 26. In some implementations, the slope angle may be between approximately 35° and 45°. Referring to FIG. 1, when the vessel 26 is coupled to the box assembly 12, the BSFL may exit the vessel 26 and enter the box assembly 12. If there is a body or a portion of a body in the box assembly 12, the BSFL may begin to decompose the body or the portion of the body. Referring to FIG. 1, when the vessel 26 is coupled to the box assembly 12, the BSFL may exit the vessel 26 and enter the box assembly 12. If there is a body or a portion of a body in the box assembly 12, the BSFL may begin to decompose the body or the portion of the body. To escape the heat produced by the decomposing body, the BSFL may be motivated to exit the second chamber 20 of the box cavity 15. In some implementations, the second chamber 20 has slanted walls with a slope angle so as to allow the BSFL to escape the second chamber 20 and then be collected in the bottom of the first chamber 19 of the box cavity 15.

In some implementations, the vessel 26 may include multiple structures. For example, the BSFL may self-harvest from a first structure of the vessel 26 into a second vessel of the vessel 26 using an escape ramp having an angle of no more than 60°. The BSFL may then exit the second structure and enter the box assembly 12.

Figure 2:
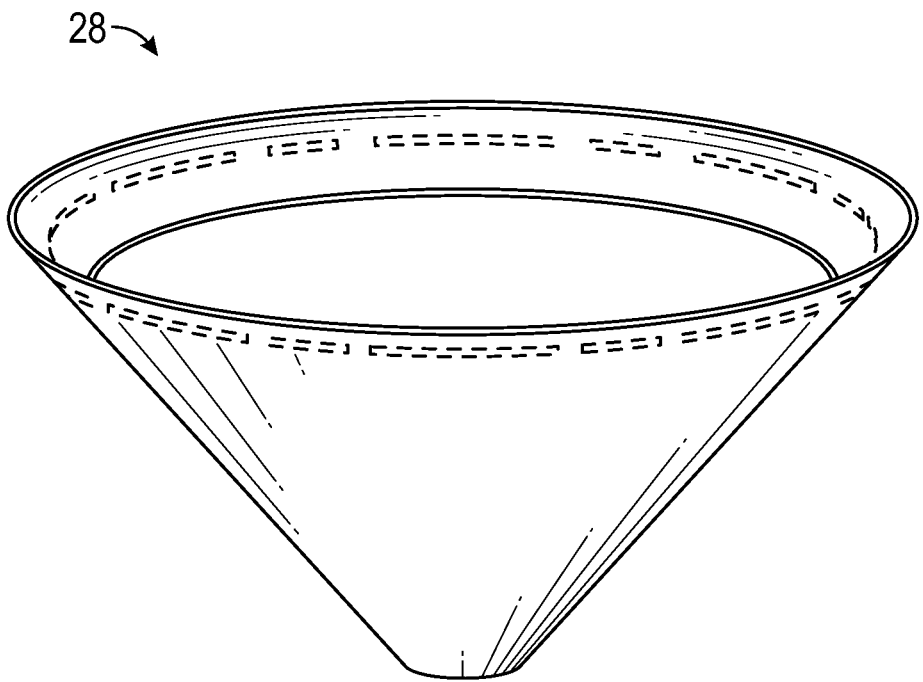
FIG. 2 depicts an embodiment of a composting bin disposed in the vessel as described in FIG. 1.

In some implementations, the vessel 26 may include a composting bin disposed therein for harvesting the BSFL. FIG. 2 depicts an example of the composting bin disposed in the vessel 26. The composting bin 28 may include dual walls for retaining heat in the vessel 26. An example of a design for the composting bin 28 is described in U.S.

application Ser. No. 29/624,567, the disclosure of which is hereby incorporated by reference in its entirety. The composting bin 28 and/or the vessel 26 may be in other shapes or sizes. In some implementations, the composting bin may be the vessel 26 as described herein.

The vessel 26 may have a controlled temperature level and/or humidity level suitable for the BSFL to self-harvest there within. In some implementations, the temperature level in the vessel 26 may be controlled to be between approximately 75 degrees Fahrenheit (° F.) and 95° F., or any other desired temperature levels. In other implementations, the temperature level in the vessel 26 may be controlled to be between approximately 65° F. and 100° F.

Referring to FIG. 1, when the vessel 26 is coupled to the box assembly 12, an operator may adjust the conditions (e.g., a temperature level, a humidity level, and/or an amount of air) inside the box assembly 12 as well as in the vessel 26 via the electronic control panel 24 so as to provide a suitable condition for the BSFL to self-harvest in the vessel 26. In some implementations, the temperature level may be set in a range of approximately 65° F. and 100° F., or at any other desired temperature levels. The BSFL may, out of its nature, self-harvest in the vessel 26. The BSFL may exit the vessel 26 and enter the box assembly 12 through the channel created by the first orifice 29 and the second orifice 30. When the BSFL are present in the box assembly 12, they may begin to decompose the at least one body or a portion of the body stored in the box assembly 12. The BSFL may consume bone marrows of the body or the portion of the body. Depending on the amount of the BSFL available in the box assembly 12, the conditions within the box assembly 12, and the size of the body or the portion of the body, the decomposition may last for a few days. After the decomposition is completed, remains of the body or the portion of the body may be removed from the box assembly 12 and returned to family members. The remains may also be donated to science for research studies, planted in the ground (e.g., in a garden), or fed to chicken, fish, birds, or the like. Comparing with the traditional cremation that uses fire, the system 10 described herein for decomposing bodies offers green cremation, which is a gentle, eco-friendly, and carbon-neutral alternative to the flame-based cremation.

Although the system 10 as described herein includes one box assembly for green cremation as illustrated herein, more than one such box assemblies may be connected, either side-by-side or end-to-end, when in use. When more than one such box assemblies are connected, each box assembly may use its own electronic control panel and air conditioner to control the conditions there within as well as the conditions in any vessels coupled thereto. Alternatively, the conditions of several such connected box assemblies and any vessels coupled thereto may be controlled by a common electronic control panel and a common air conditioner. Furthermore, when more than one such box assemblies are connected, each box assembly may be coupled by at least one vessel containing BSFL. Alternatively, several such connected box assemblies may share the BSFL coming from one or more common vessel coupled to those box assemblies.

FIG. 3A depicts a schematic perspective view of the box assembly of the system as described in FIG. 1. As shown in FIG. 3A, the first orifice 29 is provided on the side wall 16 of the box assembly 12. The first orifice 29 may be configured for the BSFL to enter the box assembly 12 for decomposing a body or a portion of a body. As discussed in FIG. 1, when more than one vessels are coupled to the side wall 16 of the box assembly 12, the box assembly 12 may include more than one orifices on the side wall 16 thereof to accommodate the orifices on those vessels.

FIG. 3B depicts a schematic perspective view of the vessel as described in FIG. 1. The vessel 26 may contain BSFL. The vessel 26 may include a shape and a size to allow the BSFL to self-harvest there within. For example, the vessel 26 may include a shape and a size to allow the BSFL to establish one or more colonies there within. The vessel 26 may include a slanted wall having a slope angle so as to allow the BSFL to exit the vessel 26. In some implementations, the slope angle may be between approximately 35° and 45°. When the vessel 26 is coupled to the box assembly 12, the BSFL may exit the vessel 26 and enter the box assembly 12. If there is a body or a portion of a body in the box assembly 12, the BSFL may begin to decompose the body or the portion of the body. In one or more implementations, the vessel 26 may include a composting bin disposed therein for harvesting the BSFL, as illustrated in FIG. 2. In some implementations, the composting bin may be the vessel 26 as described herein.

FIG. 3B shows that the second orifice 30 is provided on the vessel 26. When the vessel 26 is coupled to the box assembly 12, the BSFL may exit the vessel 26 via the second orifice 30 and enter the box assembly 12 through the first orifice 29 provided on the at least side wall 16 of the box assembly 12. As discussed in FIG. 1, the vessel 26 may include more than one orifices in addition to the second orifice 30.

FIG. 3C depicts a schematic isometric view of the box assembly of the system as described in FIG. 1. As shown in FIG. 3C, the insert 18 may be disposed within the box cavity 15, which separates the box cavity 15 into the first chamber 19 and the second chamber 20. The insert 18 may be disposed at any location within the box cavity 15. In some implementations, the insert 18 may be connected to the side wall 16 of the box 14. In some other implementations, the insert 18 may be connectable to the side wall 16 of the box 14, in which case the insert 18 may be removable or replaceable. FIG. 3C further shows that the air conditioner 32 may be disposed in the first chamber 19. The air conditioner 32 may be configured to control a temperature level and/or humidity level in the box cavity 15 when the air conditioner 32 is in operation. For example, during the decomposition process, the temperature level within the box 14 may rise. The air conditioner 32 may thus be controlled to operate to maintain the temperature level within the desired temperature range as described herein. The second chamber 20 may include a shape and a size to receive a body or a portion of a body for green cremation. In addition, FIG. 3C shows that the first orifice 29 is provided on the side wall 16 of the box assembly 12 for the BSFL entering the box assembly 12 from the vessel 26 when the vessel 26 is coupled to the side wall 16 of the box assembly 12.

Figure 4:
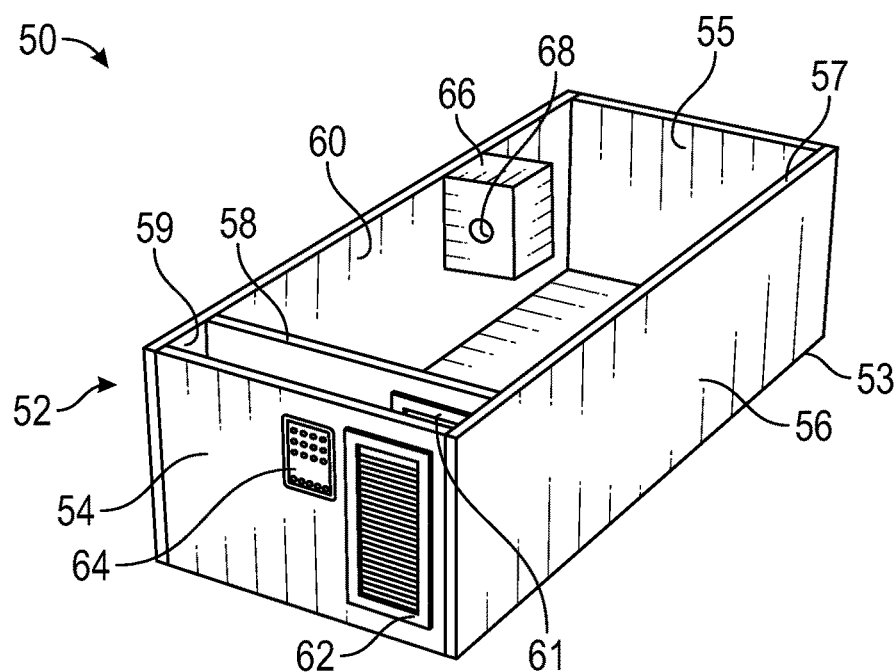
FIG. 4 depicts a schematic perspective view of a system for green cremation according to a second embodiment of the present disclosure.

FIG. 4 depicts a schematic perspective view of a system for green cremation according to a second implementation of the present disclosure. The system 50 may be positioned in an environment whose conditions are controllable. The conditions of the environment may include parameters such as a temperature level, a humidity level, a moisture level, and odors. For example, the environment may be controlled to maintain at a certain temperature and/or humidity level as desired. In FIG. 4, the system 50 may include a box assembly 52 for storing a body or a portion of a body. The body may be a human body, a non-human (e.g., dog or cat) body, or an organ from a human or non-human body. The box assembly 52 may include a box 54 defining a box cavity 55 within the box. The box 54 may further include a bottom end 53 (e.g., a base), a top end 57 defining a box opening connected to the box cavity 55, and at least one side wall (e.g., side wall 56) extending from the bottom end 53 to the top end 57. The side wall 56 at least partially defines the box cavity 55. The side wall 56 may be made of a thermal insulation material. Although FIG. 4 depicts that the shape of the box assembly 52 is rectangular, it is contemplated that in one or more implementations of the present disclosure, the box assembly 52 may be in any other desired geometric shapes, including, but not limited to, round, square, oval, or polygonal. The box assembly 52 may further include a size to receive a body or a portion of the body therein.

As shown in FIG. 4, the box assembly 52 may further include an insert 58 disposed within the box cavity 55, which separates the box cavity 55 into a first chamber 59 and a second chamber 60. The insert 58 may be disposed at any location within the box cavity 55. In some implementations, the insert 58 may be connected to the side wall 56 of the box 54. In some other implementations, the insert may be connectable to the side wall 56 of the box 54, in which case the insert 58 may be removable or replaceable. As shown in FIG. 4, the insert 58 may include an airway 61 through which air in the box cavity 55 may flow from the first chamber 59 to the second chamber 60, or vice versa. The airway 61 may be an opening disposed in the insert 58. In some implementations, a vent may be used to cover the opening and allow for the air in the box cavity 55 to flow between the first chamber 59 and the second chamber 60. The box assembly 52 may further include an air conditioner (similar to 32 in FIG. 3C) disposed in the first chamber 59. The air conditioner may be configured to control a temperature level and/or a humidity level in the box cavity 55 when it is in operation. In some implementations, the air conditioner may include one or more devices that control other environmental conditions within the box cavity 55 (e.g., moisture control and odors). The second chamber 60 may include a shape and a size to receive a body or a portion of a body for green cremation.

Referring to FIG. 4, the box assembly 52 may further include an air vent 62 disposed on the side wall 56 of the box 54 thereof. The air vent 62 may allow air to be exchanged between the box cavity 55 and the environment in which the system is situated. For example, the air vent 62 may be configured for the air inside the box cavity 55 to exit the box assembly 52 or may be configured for the air in the environment to enter the box assembly 52.

In some implementations, the box assembly 52 may further include an ozone generator disposed on the side wall 56 of the box 54. The ozone generator (not shown) may be configured to remove odors from the box cavity 55. For example, the ozone generator may be disposed in an exhaust chamber with a one-way air valve. In such an implementation, the ozone generator is configured to remove odors from the box assembly 52 without exposing the insects in the box assembly 52 to ozone.

The box assembly 52 may also include an electronic control panel 64 connected thereto and configured to control the operation of the system 50, including the operation of the air conditioner. In some implementations, the electronic control panel 64 may be connected to the side wall 56 of the box 54. According to one or more implementations of the present disclosure, the electronic control panel 64 may be a display interface, through which an operator may input operating instructions to the system 50 for the purpose of controlling the conditions (e.g., a temperature level, a humidity level, or an air amount) within the box assembly 52. Upon a request by the operator, the electronic control panel 64 may display images or videos showing a scene of the box cavity 55. This allows the operator to monitor the operation of the system 50 in real time or near rear time. The electronic control panel 64 may further electronically communicate with a remote server, such as a remote storage cloud, a remote control center, or a mobile phone of the operator or of any person of interest (e.g., a family member of the body or the portion of the body). The electronic control panel 64 may also, by wires or wirelessly, connect to at least one another electronic control panel of another system of this kind. The connection between or among such systems may provide additional features, including, but not limited to, data sharing between or among the systems, remote controls of the systems, or alert notifications among the systems. For example, if there is a technical problem with one of the connected systems, the system having the technical problem may generate an alert, which may be sent to other connected systems or to a technician or an operator who may then fix the technical problem.

The electronic control panel 64 may also leverage the Internet of Things (IoT), Bluetooth, or Wi-Fi to remotely connect to, enable, and control one or more functionalities of the system 50. For example, the electronic control panel 64 may be configured to present a display interface on a remote device, through which a user may input operating instructions to the system 50 for the purpose of controlling the conditions within the box assembly 52 (e.g., a temperature, a humidity level, or an air amount).

To carry out green cremation according to this embodiment of the present disclosure, the system 50 may further include a vessel 66 coupled to the side wall 56 of the box assembly 52. In some implementations, the vessel 66 may be glued, screwed, or hooked to the side wall 56 of the box assembly 52, or any other desired coupling mechanisms.

As shown in FIG. 4, the vessel 66 may be coupled to an inner surface of the side wall 56 of the box assembly 52. In some implementations, the vessel 66 may be integrated with the box assembly 52. In some other implementations, the vessel 66 may be removably attached to the box assembly 52. It is contemplated that although FIG. 4 shows one vessel coupled to the side wall 56 of the box assembly 52, more than one vessels may be similarly coupled thereto. It is further contemplated that although FIG. 4 shows that the vessel 66 is coupled into the second chamber 60, the vessel 66 may also be coupled into the first chamber 59. The vessel 66 may include an orifice 68, which may be configured for BSFL to exit the vessel 66 to decompose the body or the portion of the body stored in the box assembly 52. In some implementations, the vessel 66 may include more than one orifices in addition to the orifice 68 shown in FIG. 4.

The vessel 66 may contain BSFL. The vessel 66 may include a shape and a size to allow the BSFL to self-harvest there within, as described herein. For example, the vessel 66 may include a shape and a size to allow the BSFL to establish one or more colonies there within. The vessel 66 may include a slanted wall having a slope angle so as to allow the BSFL to exit the vessel 66. In some implementations, the slope angle may be between approximately 35° and 45°. Referring to FIG. 4, when the vessel 66 is coupled to the box assembly 52, the BSFL may exit the vessel 66 and enter the box assembly 52. If there is a body or a portion of a body in the box assembly 52, the BSFL may begin to decompose the body or the portion of the body. To escape the heat produced by the decomposing body, the BSFL may be motivated to exit the second chamber 60 of the box cavity 55. In some implementations, the second chamber 60 has slanted walls with a slope angle so as to allow the BSFL to escape the second chamber 60 and then be collected in the bottom of the first chamber 59 of the box cavity 55.

In some implementations, the vessel 66 may include multiple structures. For example, the BSFL may self-harvest from a first structure of the vessel 66 into a second vessel of the vessel 66 using an escape ramp having an angle of no more than 60°. The BSFL may then exit the second structure and enter the box assembly 52.

In some implementations, the vessel 66 may include a composting bin disposed therein for harvesting the BSFL. The composting bin may include dual walls for retaining heat in the vessel 26, as illustrated in FIG. 2. The composting bin and/or the vessel 66 may be in other shapes or sizes. In some implementations, the composting bin may be the vessel 66 as described herein.

The vessel 66 may have a controlled temperature level and/or humidity level suitable for the BSFL to self-harvest there within. In some implementations, the temperature level in the vessel 66 may be controlled to be between approximately 75° F. and 95° F., or any other desired temperature levels. In other implementations, the temperature level in the vessel 66 may be controlled to be between approximately 65° F. and 100° F.

Referring to FIG. 4, when the vessel 66 is coupled to the box assembly 52, an operator may adjust the conditions (e.g., a temperature level, a humidity level, and/or an amount of air) inside the box assembly 52 as well as in the vessel 66 via the electronic control panel 64 so as to provide a suitable condition for the BSFL to self-harvest in the vessel 66. In some implementations, the temperature level may be set in a range of approximately 65° F. and 100° F., or at any other desired temperature levels. The BSFL may, out of its nature, self-harvest in the vessel 66. The BSFL may exit the vessel 66 and enter the box assembly 52 through the orifice 68. When the BSFL are present in the box assembly 52, they may begin to decompose the body or the portion of the body stored in the box assembly 52. The BSFL may consume bone marrows of the body or the portion of the body. Depending on the amount of the BSFL available in the box assembly 52, the conditions within the box assembly 52, and the size of the body or the portion of the body, the decomposition may last for a few days or a week or more. After the decomposition is completed, remains of the body or the portion of the body may be removed from the box assembly 52 and returned to family members. The remains may also be donated to science for research studies, planted in the ground (e.g., in a garden), or fed to chicken, fish, birds, or the like. Comparing with the traditional cremation that uses fire, the system 50 described herein for decomposing bodies offers green cremation, which is a gentle, eco-friendly, and carbon-neutral alternative to the flame-based cremation.

Although the system 50 as described herein includes one box assembly for green cremation as illustrated herein, more than one such box assemblies may be connected, either side-by-side or end-to-end, when in use. When more than one such box assemblies are connected, each box assembly may use its own electronic control panel and air conditioner to control the conditions there within as well as the conditions in any vessels coupled thereto. Alternatively, the conditions of several such connected box assemblies and any vessels coupled thereto may be controlled by a common electronic control panel and a common air conditioner. Furthermore, when more than one such box assemblies are connected, each box assembly may be coupled to at least one vessel containing BSFL. Alternatively, several such connected box assemblies may share the BSFL coming from one or more common vessel coupled to those box assemblies.

Figure 5:
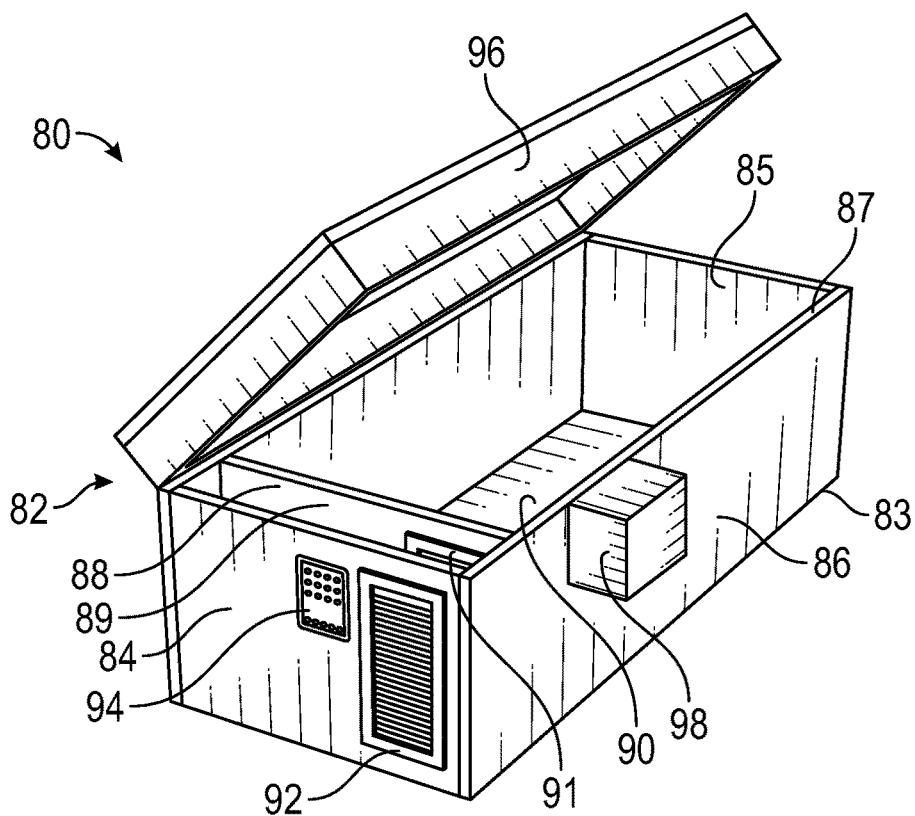
FIG. 5 depicts a schematic perspective view of a system for green cremation according to a third embodiment of the present disclosure.

FIG. 5 depicts a schematic perspective view of a system for green cremation according to a third implementation of the present disclosure. As shown in FIG. 5, the system 80 may include a box assembly 82 for storing a body or a portion of a body. The body may be a human body, a non-human (e.g., dog or cat) body, or an organ from a human or non-human body. The box assembly 82 may include a box 84 defining a box cavity 85 within the box. The box 84 may further include a bottom end 83 (e.g., a base), a top end 87 defining a box opening connected to the box cavity 85, and at least one side wall (e.g., side wall 86) extending from the bottom end 83 to the top end 87. The side wall 86 at least partially defines the box cavity 85. The side wall 86 may be made of a thermal insulation material. Although FIG. 5 depicts that the shape of the box assembly 82 is rectangular, it is contemplated that in one or more implementations of the present disclosure, the box assembly 82 may be in any other desired geometric shapes, including, but not limited to, round, square, oval, or polygonal. The box assembly 82 may further include a size to receive a body or a portion of a body therein.

As shown in FIG. 5, the box assembly 82 may further include an insert 88 disposed within the box cavity 85, which separates the box cavity 85 into a first chamber 89 and a second chamber 90. The insert 88 may be disposed at any location within the box cavity 85. In some implementations, the insert 88 may be connected to the side wall 86 of the box 84. In some other implementations, the insert 88 may be connectable to the side wall 86 of the box 84, in which case the insert 88 may be removable or replaceable. As shown in FIG. 5, the insert 88 may include an airway 91 through which air in the box cavity 85 may flow from the first chamber 89 to the second chamber 90, or vice versa. The airway 91 may be an opening disposed in the insert 88. In some implementations, a vent may be used to cover the opening and allow for the air in the box cavity 85 to flow between the first chamber 89 and the second chamber 90. The box assembly 82 may further include an air conditioner 104 (see FIG. 6C) disposed in the first chamber 89. The air conditioner 104 may be configured to control a temperature level and/or a humidity level in the box cavity 85 when it is in operation. In some implementations, the air conditioner 104 may include one or more devices that control other environmental conditions within the box cavity 85 (e.g., moisture control and odors). The second chamber 90 may include a shape and a size to receive a body or a portion of a body for green cremation.

Referring to FIG. 5, the box assembly 82 may further include an air vent 92 disposed on the side wall 86 of the box 84 thereof. The air vent 92 may allow air to be exchanged between the box cavity 85 and an ambient environment (i.e. outside the system 80). For example, the air vent may be configured for the air inside the box cavity 85 to exit the box assembly 82 or may be configured for the air in the ambient environment to enter the box assembly 82.

In some implementations, the box assembly 82 may further include an ozone generator disposed on the side wall 86 of the box 84. The ozone generator (not shown) may be configured to remove odor from the box cavity 85. For example, the ozone generator may be disposed in an exhaust chamber with a one-way air valve. In such an implementation, the ozone generator is configured to remove odors from the box assembly 82 without exposing the insects in the box assembly 82 to ozone.

The box assembly 82 may also include an electronic control panel 94 connected thereto and configured to control the operation of the system 80, including the operation of the air conditioner. In some implementations, the electronic control panel 94 may be connected to the side wall 86 of the box 84. According to one or more implementations of the present disclosure, the electronic control panel 94 may be a display interface, through which an operator may input operating instructions to the system 80 for the purpose of controlling the conditions (e.g., a temperature level, a humidity level, or an air amount) within the box assembly 82. Upon a request by the operator, the electronic control panel 94 may display images or videos showing a scene of the box cavity 85. This allows the operator to monitor the operation of the system 80 in real time or near real time. The electronic control panel 94 may further electronically communicate with a remote server, such as a remote storage cloud, a remote control center, or a mobile phone of the operator or of any person of interest (e.g., a family member of the body or the portion of the body). The electronic control panel 94 may also, by wires or wirelessly, connect to at least one another electronic control panel of another system of this kind. The connection between or among such systems may provide additional features, including, but not limited to, data sharing between or among the systems, remote controls of the systems, or alert notifications among the systems. For example, if there is a technical problem with one of the connected systems, the system having the technical problem may generate an alert, which may be sent to other connected systems or to a technician or an operator who may then fix the technical problem.

The electronic control panel 94 may also leverage the Internet of Things (IoT), Bluetooth, or Wi-Fi to remotely connect to, enable, and control one or more functionalities of the system 80. For example, the electronic control panel 94 may be configured to present a display interface on a remote device, through which a user may input operating instructions to the system 80 for the purpose of controlling the conditions within the box assembly 82 (e.g., a temperature, a humidity level, or an air amount).

Referring to FIG. 5, the system 80 may further include a cover 96 which may cover or uncover the box opening of the box 84 of the box assembly 82 thereof. In some implementations, the cover 96 may be hingedly connected to the top end 87 of the box 84. In some other implementations, the cover 96 may be removably disposed onto the top end 87 of the box 84. The system 80 may be in an open state when the cover 96 uncovers the box cavity 85. When the system 80 is in the open state, the operator may place a body or a portion of a body into the box assembly 82 (e.g., in the second chamber). The system 80 may be in a closed state when the cover 96 covers the box cavity 85. When the system 80 is in the closed state, the operator may input operating instructions to the system 80 to control the conditions (e.g., a temperature level, a humidity level, or an air amount) within the box assembly 82 for green cremation.

To carry out green cremation according to this embodiment of the present disclosure, the system 80 may further include a vessel 98 coupled to the side wall 86 of the box assembly 82. In some implementations, the vessel 98 may be glued, screwed, or hooked to the side wall 86 of the box assembly, or any other desired coupling mechanisms.

As shown in FIG. 5, the vessel 98 may be coupled to an outer surface of the side wall 86 of the box assembly 82. In some implementations, the vessel 98 may be integrated with the box assembly 82. In some other implementations, the vessel 98 may be removably attached to the box assembly 82. It is contemplated that although FIG. 5 shows one vessel coupled to the side wall 86 of the box assembly 82, more than one vessels may be similarly coupled thereto. The box assembly 82 may include a first orifice 100 (see FIG. 6A) on the side wall 86 of the box 84 thereof. The vessel 98 may include a second orifice 102 (see FIG. 6B), which may, with the first orifice 100, form a channel between the vessel 98 and the box assembly 82 when the vessel 98 is coupled to the box assembly 82. It is further contemplated that when more than one vessels coupled to the side wall 86 of the box assembly 82, the box assembly 82 may include more than one orifices on the side wall 86 thereof to accommodate the orifices on those vessels. In some other implementations, the vessel 98 may include more than one orifices in addition to the second orifice 102.

The vessel 98 may contain BSFL. The vessel 98 may include a shape and a size to allow the BSFL to self-harvest there within, as described herein. For example, the vessel 98 may include a shape and a size to allow the BSFL to establish one or more colonies there within. The vessel 98 may include a slanted wall having a slope angle so as to allow the BSFL to exit the vessel 98. In some embodiments, the slope angle may be between approximately 35° and 45°. Referring to FIG. 5, when the vessel 98 is coupled to the box assembly 82, the BSFL may exit the vessel 98 and enter the box assembly 82. If there is a body or a portion of a body in the box assembly 82, the BSFL may begin to decompose the body or the portion of the body. To escape the heat produced by the decomposing body, the BSFL may be motivated to exit the second chamber 90 of the box cavity 85. In some implementations, the second chamber 90 has slanted walls with a slope angle so as to allow the BSFL to escape the second chamber 90 and then be collected in the bottom of the first chamber 89 of the box cavity 85.

In some implementations, the vessel 98 may include multiple structures. For example, the BSFL may self-harvest from a first structure of the vessel 98 into a second vessel of the vessel 98 using an escape ramp having an angle of no more than 60°. The BSFL may then exit the second structure and enter the box assembly 82.

In one or more implementations, the vessel 98 may include a composting bin disposed therein for harvesting the BSFL. The composting bin may include dual walls for retaining heat in the vessel 98, as illustrated in FIG. 2. The composting bin and/or the vessel 98 may be in other shapes or sizes. In some implementations, the composting bin may be the vessel 98 as described herein.

The vessel 98 may have a controlled temperature level and/or humidity level suitable for the BSFL to self-harvest there within. In some implementations, temperature level in the vessel 98 may be controlled to be between approximately 75° F. and 95° F., or any other desired temperature levels. In other implementations, the temperature level in the vessel 98 may be controlled to be between approximately 65° F. and 100° F.

Referring to FIG. 5, when the vessel 98 is coupled to the box assembly 82, an operator may adjust the conditions (e.g., a temperature level, a humidity level, and/or an amount of air) inside the box assembly 82 as well as in the vessel 98 via the electronic control panel 94 so as to provide a suitable condition for the BSFL to self-harvest in the vessel 98. In some implementations, the temperature level may be set in a range of approximately 65° F. and 100° F., or at any other desired temperature levels. The BSFL may, out of its nature, self-harvest in the vessel 98. The BSFL may exit the vessel 98 and enter the box assembly 82 through the channel created by the first orifice 100 and the second orifice 102.

When the BSFL are present in the box assembly 82, they may begin to decompose a body or a portion of a body stored in the box assembly 82. The BSFL may consume bone marrows of the body or the portion of the body. Depending on the amount of the BSFL available in the box assembly 82, the conditions within the box assembly 82, and the size of the body or the portion of the body, the decomposition may last for a few days. After the decomposition is completed, remains of the body or the portion of the body may be removed from the box assembly 82 and returned to family member. The remains may also be donated to science for research studies, planted in the ground (e.g., in a garden), or fed to chicken, fish, birds, or the like. Comparing with the traditional cremation that uses fire, the system 80 described herein for decomposing bodies offers green cremation, which is a gentle, eco-friendly, and carbon-neutral alternative to the flame-based cremation.

Although the system 80 as described herein includes one box assembly for green cremation as illustrated herein, more than one such box assemblies may be connected, either side-by-side or end-to-end, when in use. When more than one such box assemblies are connected, each box assembly may use its own electronic control panel and air conditioner to control the conditions there within as well as the conditions in any vessels coupled thereto. Alternatively, the conditions of several such connected box assemblies and any vessels coupled thereto may be controlled by a common electronic control panel and a common air conditioner. Furthermore, when more than one such box assemblies are connected, each box assembly may be coupled to at least one vessel containing BSFL. Alternatively, several such connected box assemblies may share the BSFL coming from one or more common vessel coupled to those box assemblies.

FIG. 6A depicts a schematic perspective view of the box assembly of the system as described in FIG. 5. As shown in FIG. 6A, the first orifice 100 is provided on the side wall 86 of the box assembly 82. The first orifice 100 may be configured for the BSFL to enter the box assembly 82 for decomposing a body or a portion of a body. As discussed in FIG. 5, when more than one vessels are coupled to the side wall 86 of the box assembly 82, the box assembly 82 may include more than one orifices on the side wall 86 thereof to accommodate the orifices on those vessels. Furthermore, FIG. 6A shows the cover 96 of the system 80. The cover 96 may cover or uncover the box opening of the box 84 of the box assembly 82. In some implementations, the cover 96 may be hingedly connected to the top end 87 of the box 84. In some other implementations, the cover 96 may be removably disposed onto the top end 87 of the box 84.

FIG. 6B depicts a schematic perspective view of the vessel as described in FIG. 5. The vessel 98 may include a shape and a size to allow the BSFL to self-harvest there within. For example, the vessel 98 may include a shape and a size to allow the BSFL to establish one or more colonies there within. The vessel 98 may include a slanted wall having a slope angle so as to allow the BSFL to exit the vessel 26. In some implementations, the slope angle may be between approximately 35° and 45°. When the vessel 98 is coupled to the box assembly 82, the BSFL may exit the vessel 98 and enter the box assembly 82. If there is a body or a portion of a body in the box assembly 82, the BSFL may begin to decompose the body or the portion of the body. In one or more implementations, the vessel 98 may include a composting bin disposed therein for harvesting the BSFL, as illustrated in FIG. 2. In some implementations, the composting bin may be the vessel 98 as described herein.

FIG. 6B shows that the second orifice 102 is provided on the vessel 98. When the vessel 98 is coupled to the box assembly 82, the BSFL may exit the vessel 98 via the second orifice 102 and enter the box assembly 82 through the first orifice 100 provided on the at least side wall 86 of the box assembly 82. As discussed in FIG. 5, the vessel 98 may include more than one orifices in addition to the second orifice 102.

FIG. 6C depicts a schematic isometric view of the box assembly of the system as described in FIG. 5. As shown in FIG. 6C, the insert 88 may be disposed within the box cavity 85, which separates the box cavity 85 into the first chamber 89 and the second chamber 90. The insert 88 may be disposed at any location within the box cavity 85. In some implementations, the insert 88 may be connected to the side wall 86 of the box 84. In some other implementations, the insert 88 may be connectable to the side wall 86 of the box 84, in which case the insert 88 may be removable or replaceable. FIG. 6C further shows that the air conditioner 104 may be disposed in the first chamber 89. The air conditioner 104 may be configured to control a temperature level and/or humidity level in the box cavity 85 when the air conditioner 104 is in operation. For example, during the decomposition process, the temperature level within the box 84 may rise. The air conditioner 104 may thus be controlled to operate to maintain the temperature level within the desired temperature range as described herein. The second chamber 90 may include a shape and a size to receive a body or a portion of a body for green cremation. In addition, FIG. 6C shows the first orifice 100 is provided on the side wall 86 of the box assembly 82 for the BSFL entering the box assembly 82 from the vessel 98 when the vessel 98 is coupled to the side wall 86 of the box assembly 82. Furthermore, FIG. 6C shows the cover 96 of the system 80. The cover 96 may cover or uncover the box opening of the box 84 of the box assembly 82. In some implementations, the cover 96 may be hingedly connected to the top end 87 of the box 84. In some other implementations, the cover 96 may be removably disposed onto the top end 87 of the box 84.

Figure 7:
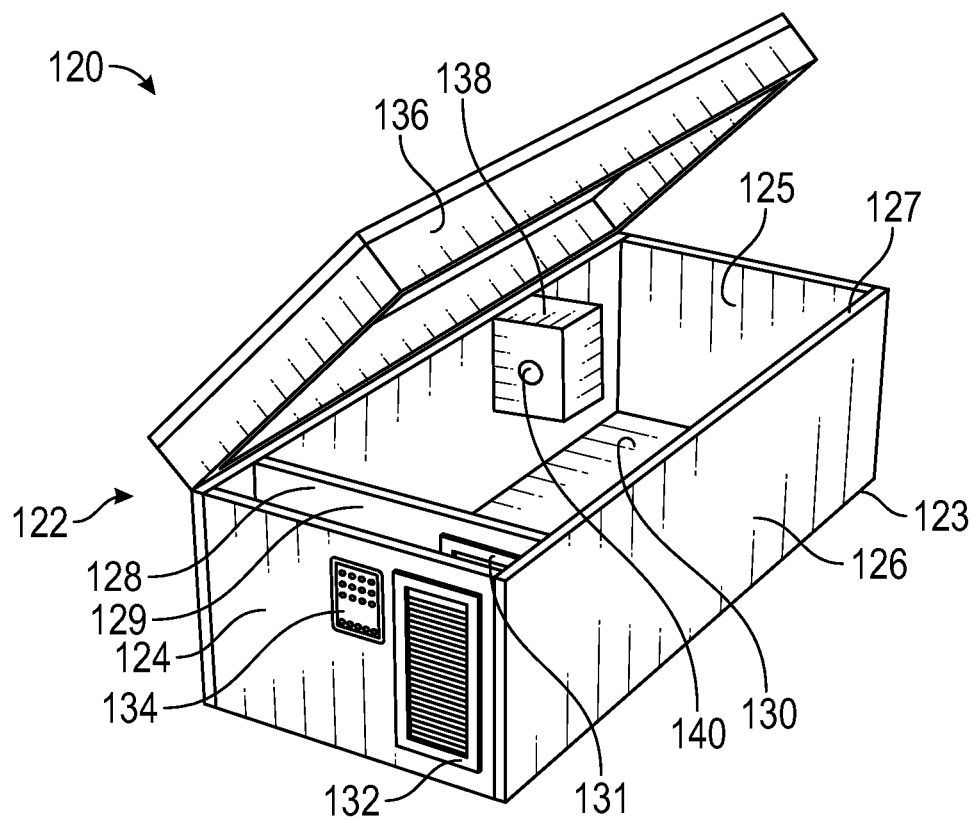
FIG. 7 depicts a schematic perspective view of a system for green cremation according to a fourth embodiment of the present disclosure.

FIG. 7 depicts a schematic perspective view of a system for green cremation according to a fourth embodiment of the present disclosure. As shown in FIG. 7, the system 120 may include a box assembly 122 for storing a body or a portion of a body. The body may be a human body, a non-human (e.g., dog or cat) body, or an organ from a human or non-human body. The box assembly 122 may include a box 124 defining a box cavity 125 within the box 124. The box 124 may further include a bottom end 123 (e.g., a base), a top end 127 defining a box opening connected to the box cavity 125, and at least one side wall (e.g., side wall 126) extending from the bottom end 123 to the top end 127. The side wall 126 at least partially defines the box cavity 125. The side wall 126 may be made of a thermal insulation material. Although FIG. 7 depicts that the shape of the box assembly 122 is rectangular, it is contemplated that in one or more implementations of the present disclosure, the box assembly 122 may be in any other desired geometric shapes, including, but not limited to, round, square, oval, or polygonal. The box assembly 122 may further include a size to receive a body or a portion of a body therein.

As shown in FIG. 7, the box assembly 122 may further include an insert 128 disposed within the box cavity 125, which separates the box cavity 125 into a first chamber 129 and a second chamber 130. The insert 128 may be disposed at any location within the box cavity 125. In some implementations, the insert 128 may be connected to the side wall 126 of the box 124. In some other implementations, the insert 128 may be connectable to the side wall 126 of the box 124, in which case the insert 128 may be removable or replaceable. As shown in FIG. 7, the insert 128 may include an airway 131 through which air in the box cavity 125 may flow from the first chamber 129 to the second chamber 130, or vice versa. The airway 131 may be an opening disposed in the insert 128. In some implementations, a vent may be used to cover the opening and allow for the air in the box cavity 125 to flow between the first chamber 129 and the second chamber 130. The box assembly 122 may further include an air conditioner (similar to 104 in FIG. 6C) disposed in the first chamber 129. The air conditioner may be configured to control a temperature level and/or a humidity level in the box cavity 125 when it is in operation. In some implementations, the air conditioner may include one or more devices that control other environmental conditions within the box cavity 125 (e.g., moisture control and odors). The second chamber 130 may include a shape and a size to receive a body or a portion of a body for green cremation.

Referring to FIG. 7, the box assembly 122 may further include an air vent 132 disposed on the side wall 126 of the box 124 thereof. The air vent 132 may allow air to be exchanged between the box cavity 125 and an ambient environment (i.e. outside the system 120). For example, the air vent 132 may be configured for the air inside the box cavity 125 to exit the box assembly 122 or may be configured for the air in the ambient environment to enter the box assembly 122.

In some implementations, the box assembly 122 may further include an ozone generator disposed on the side wall 126 of the box 124. The ozone generator (not shown) may be configured to remove odors from the box cavity 125. For example, the ozone generator may be disposed in an exhaust chamber with a one-way air valve. In such an implementation, the ozone generator is configured to remove odors from the box assembly 122 without exposing the insects in the box assembly 122 to ozone.

The box assembly 122 may also include an electronic control panel 134 connected thereto and configured to control the operation of the system 120, including the operation of the air conditioner. In some implementations, the electronic control panel 134 may be connected to the side wall 126 of the box 124. According to one or more implementations of the present disclosure, the electronic control panel 134 may be a display interface, through which an operator may input operating instructions to the system 120 for the purpose of controlling the conditions (e.g., a temperature level, a humidity level, or an air amount) within the box assembly 122. Upon a request by the operator, the electronic control panel 134 may display images or videos showing a scene of the box cavity 125. This allows the operator to monitor the operation of the system 120 in real time or near real time. The electronic control panel 134 may further electronically communicate with a remote server, such as a remote storage cloud, a remote control center, or a mobile phone of the operator or of any person of interest (e.g., a family member of the body or the portion of the body). The electronic control panel 134 may also, by wires or wirelessly, connect to at least one another electronic control panel of another system of this kind. The connection between or among such systems may provide additional features, including, but not limited to, data sharing between or among the systems, remote controls of the systems, or alert notifications among the systems. For example, if there is a technical problem with one of the connected systems, the system having the technical problem may generate an alert, which may be sent to other connected systems or to a technician or an operator who may then fix the technical problem.

The electronic control panel 134 may also leverage the Internet of Things (IoT), Bluetooth, or Wi-Fi to remotely connect to, enable, and control one or more functionalities of the system 120. For example, the electronic control panel 134 may be configured to present a display interface on a remote device, through which a user may input operating instructions to the system 120 for the purpose of controlling the conditions within the box assembly 122 (e.g., a temperature, a humidity level, or an air amount).

Referring to FIG. 7, the system 120 may further include a cover 136 which may cover or uncover the box opening of the box 124 of the box assembly 122 thereof. In some implementations, the cover 136 may be hingedly connected to the top end 127 of the box 124. In some other implementations, the cover 136 may be removably disposed onto the top end 127 of the box 124. The system 120 may be in an open state when the cover 136 uncovers the box cavity 125. When the system 120 is in the open state, the operator may place a body or a portion of the body into the box assembly 122 (e.g., the second chamber). The system 120 may be in a closed state when the cover 136 covers the box cavity 125. When the system 120 is in the closed state, the operator may input operating instructions to the system 120 to control the conditions (e.g., a temperature level, a humidity level, or an air amount) within the box assembly 122 for green cremation.

To carry out green cremation according to this embodiment of the present disclosure, the system 120 may further include a vessel 138 coupled to the side wall 126 of the box assembly 122. In some implementations, the vessel 138 may be glued, screwed, or hooked to the side wall 16 of the box assembly, or any other desired coupling mechanisms.

As shown in FIG. 7, the vessel 138 may be coupled to an inner surface of the side wall 126 of the box assembly 122. In some implementations, the vessel 138 may be integrated with the box assembly 122. In some other implementations, the vessel 138 may be removably attached to the box assembly 122. It is contemplated that although FIG. 7 shows one vessel coupled to the side wall 126 of the box assembly 122, more than one vessels may be similarly coupled thereto. It is further contemplated that although FIG. 7 shows that the vessel 138 is coupled into the second chamber 130, the vessel 138 may also be coupled into the first chamber 129. The vessel 138 may include an orifice 140, which may be configured for BSFL to exit the vessel 138 to decompose the body or the portion of the body stored in the box assembly 122. In some implementations, the vessel 138 may include more than one orifices in addition to the orifice 140 shown in FIG. 7.

The vessel 138 may contain BSFL. The vessel 138 may include a shape and a size to allow the BSFL to self-harvest there within. For example, the vessel 138 may include a shape and a size to allow the BSFL to establish one or more colonies there within. The vessel 138 may include a slanted wall having a slope angle so as to allow the BSFL to exit the vessel 138. In some implementations, the slope angle may be between approximately 35° and 45°. Referring to FIG. 7, when the vessel 138 is coupled to the box assembly 122, the BSFL may exit the vessel 138 and enter the box assembly 122. If there is a body or a portion of a body in the box assembly 122, the BSFL may begin to decompose the body or the portion of the body. To escape the heat produced by the decomposing body, the BSFL may be motivated to exit the second chamber 130 of the box cavity 125. In some implementations, the second chamber 130 has slanted walls with a slope angle so as to allow the BSFL to escape the second chamber 130 and then be collected in the bottom of the first chamber 129 of the box cavity 125.

In some implementations, the vessel 138 may include multiple structures. For example, the BSFL may self-harvest from a first structure of the vessel 138 into a second vessel of the vessel 138 using an escape ramp having an angle of no more than 60°. The BSFL may then exit the second structure and enter the box assembly 122.

In one or more implementations, the vessel 138 may include a composting bin disposed therein for harvesting the BSFL. The composting bin may include dual walls for retaining heat in the vessel, as illustrated in FIG. 2. The composting bin and/or the vessel 138 may be in other shapes or sizes if necessary. In some implementations, the composting bin may be the vessel 66 as described herein.

The vessel 138 may have a controlled temperature level and/or humidity level suitable for the BSFL to self-harvest there within. In some implementations, the temperature level in the vessel 138 may be controlled to be between approximately 75° F. and 95° F., or any other desired temperature levels. In other implementations, the temperature level in the vessel 66 may be controlled to be between approximately 65° F. and 100° F.

Referring to FIG. 7, when the vessel 138 is coupled to the box assembly 122, an operator may adjust the conditions (e.g., a temperature level, a humidity level, and/or an amount of air) inside the box assembly 122 as well as in the vessel 138 via the electronic control panel 134 so as to provide a suitable condition for the BSFL to self-harvest in the vessel 138. In some implementations, the temperature level may be set in a range of approximately 65° F. and 100° F., or at any other desired temperature levels. The BSFL may, out of its nature, self-harvest in the vessel 138. When the BSFL become mature, they may exit the vessel 138 and enter the box assembly 122 through the orifice 140. When the BSFL are present in the box assembly 122, they may begin to decompose the body or the portion of the body stored in the box assembly 122. The BSFL may consume bone marrows of the body or the portion of the body. Depending on the amount of the BSFL available in the box assembly 122, the conditions within the box assembly 122, and the size of the body or the portion of the body, the decomposition may last for a few days. After the decomposition is completed, remains of the body or the portion of the body may be removed and returned to family members. The remains may also be donated to science for research studies, planted in the ground (e.g., in a garden), or fed to chicken, fish, birds, or the like. Comparing with the traditional cremation that uses fire, the system 120 described herein for decomposing bodies offers green cremation, which is a gentle, eco-friendly, and carbon-neutral alternative to the flame-based cremation.

Although the system 120 as described herein includes one box assembly for green cremation as illustrated herein, more than one such box assemblies may be connected, either side-by-side or end-to-end, when in use. When more than one such box assemblies are connected, each box assembly may use its own electronic control panel and air conditioner to control the conditions there within as well as the conditions in any vessels coupled thereto. Alternatively, the conditions of several such connected box assemblies and any vessels coupled thereto may be controlled by a common electronic control panel and a common air conditioner. Furthermore, when more than one such box assemblies are connected, each box assembly may be coupled to at least one vessel containing BSFL. Alternatively, several such connected box assemblies may share the BSFL coming from one or more common vessel coupled to those box assemblies.

No part of the description in this application should be read as implying that any particular element, step, or function is an essential element that must be included in the claim scope. The scope of patented subject matter is defined only by the claims. Moreover, none of the claims is intended to invoke 25 U.S.C. § 104(f) unless the exact words "means for" are followed by a participle.

The foregoing description, for purposes of explanation, use specific nomenclature to provide a thorough understanding of the described embodiments. However, it should be apparent to one skilled in the art that the specific details are not required to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present disclosure. Once the above disclosure is fully appreciated, numerous variations and modifications will become apparent to those skilled in the art. It is intended that the following claims be interpreted to embrace all such variations and modifications.

What is claimed is:

1. A system for cremating a deceased body, the system being situated in an environment whose conditions are controllable, the system comprising:
   a box assembly for storing the deceased body or a portion of the deceased body, the box assembly including:
      a box defining a box cavity within the box, a bottom end, a top end defining a box opening connected to the box cavity, and at least one side wall extending from the bottom end to the top end, and
      an air conditioner disposed in the box cavity and configured to control a temperature level or a humidity level in the box cavity when the air conditioner is in operation; and
   a vessel coupled to the at least one side wall of the box of the box assembly, wherein the vessel includes insect larvae that self-harvest, exit the vessel, and enter the box assembly to decompose the deceased body or the portion of the deceased body stored in the box assembly, and wherein the vessel further includes an orifice configured for the insect larvae to exit the vessel.

2. The system of claim 1, wherein the orifice is a first orifice, and wherein the at least one side wall of the box includes a second orifice that is configured for the insect larvae to enter the box assembly.

3. The system of claim 2, wherein the vessel is coupled to an outer surface of the at least one side wall of the box.

4. The system of claim 1, wherein the vessel is coupled to an inner surface of the at least one side wall of the box.

5. The system of claim 1, wherein the at least one side wall is made of a thermal insulation material.

6. The system of claim 1, wherein the temperature level is controlled to be between approximately 65° F. and 100° F.

7. The system of claim 1, wherein the box assembly further includes an insert disposed within the box cavity, the insert separating the box cavity into a first chamber and a second chamber, wherein the air conditioner is disposed in the first chamber, and the deceased body or the portion of the deceased body is stored in the second chamber.

8. The system of claim 7, wherein the insert further includes an airway through which air in the box cavity flows between the first and second chambers.

9. The system of claim 1, further comprising an electronic control panel configured to control the operation of the air conditioner.

10. A system for cremating a deceased body, the system comprising:
 a box assembly for storing the deceased body or a portion of the deceased body, the box assembly including:
  a box defining a box cavity within the box, a bottom end, a top end defining a box opening connected to the box cavity, and at least one side wall extending from the bottom end to the top end, and
  an air conditioner disposed within the box cavity and configured to control a temperature level or a humidity level in the box cavity when the air conditioner is in operation;
 a vessel coupled to the at least one side wall of the box of the box assembly, wherein the vessel includes insect larvae that self-harvest, exit the vessel, and enter the box assembly to decompose the deceased body or the portion of the deceased body stored in the box assembly, and wherein the vessel further includes an orifice configured for the insect larvae to exit the vessel; and
 a cover hingedly connected to or removably disposed onto the top end of the box of the box assembly, wherein the system is in an open state when the cover uncovers the box cavity of the box, and in a closed state when the cover covers the box cavity of the box.

11. The system of claim 10, wherein the orifice is a first orifice, and wherein the at least one side wall of the box includes a second orifice that is configured for the insect larvae to enter the box assembly.

12. The system of claim 11, wherein the vessel is coupled to an outer surface of the at least one side wall of the box.

13. The system of claim 10, wherein the vessel is coupled to an inner surface of the at least one side wall of the box.

14. The system of claim 10, wherein the at least one side wall is made of a thermal insulation material.

15. The system of claim 10, wherein the temperature level is controlled to be between approximately 65° F. and 100° F.

16. The system of claim 10, wherein the box assembly further includes an insert disposed within the box cavity, the insert separating the box cavity into a first chamber and a second chamber, wherein the air conditioner is disposed in the first chamber, and the deceased body or the portion of the deceased body is stored in the second chamber.

17. The system of claim 16, wherein the insert further includes an airway through which air in the box cavity flows between the first and second chambers.

18. The system of claim 10, further comprising an electronic control panel configured to control the operation of the air conditioner.

* * * * *